United States Patent [19]
Wijay

[11] Patent Number: 5,824,059
[45] Date of Patent: Oct. 20, 1998

[54] FLEXIBLE STENT

[76] Inventor: Bandula Wijay, 1903 Carriage Creek Dr., Friendswood, Tex. 77546

[21] Appl. No.: 906,054

[22] Filed: Aug. 5, 1997

[51] Int. Cl.$^6$ ........................................................ A61F 2/06
[52] U.S. Cl. ................................................................ 623/1
[58] Field of Search ................................... 623/1, 11, 12; 606/194, 195

[56] References Cited

U.S. PATENT DOCUMENTS

| | | |
|---|---|---|
| Re. 34,037 | 8/1992 | Innue et al. . |
| 4,503,569 | 3/1985 | Dotter . |
| 4,580,568 | 4/1986 | Gianturco . |
| 4,732,152 | 3/1988 | Wallsten et al. . |
| 4,740,207 | 4/1988 | Kreamer . |
| 4,776,337 | 10/1988 | Palmaz . |
| 4,795,458 | 1/1989 | Regan . |
| 4,820,298 | 4/1989 | Leveen et al. . |
| 4,886,062 | 12/1989 | Wiktor . |
| 4,913,141 | 4/1990 | Hillstead . |
| 4,950,227 | 8/1990 | Savin et al. . |
| 4,964,853 | 10/1990 | Sugiyama et al. . |

(List continued on next page.)

FOREIGN PATENT DOCUMENTS

| | | |
|---|---|---|
| 421729A2 | 4/1991 | European Pat. Off. . |
| 540290A2 | 5/1993 | European Pat. Off. . |
| 556850A1 | 8/1993 | European Pat. Off. . |
| 621017A1 | 10/1994 | European Pat. Off. . |
| 662307A1 | 7/1995 | European Pat. Off. . |
| 2671280A1 | 7/1992 | France . |
| 2702954A1 | 9/1994 | France . |
| WO 91/12047 | 8/1991 | WIPO . |
| WO 92/11824 | 7/1992 | WIPO . |
| WO 92/16166 | 10/1992 | WIPO . |
| WO 94/20044 | 9/1994 | WIPO . |
| WO 95/03010 | 2/1995 | WIPO . |

OTHER PUBLICATIONS

AngioStent Balloon Expandable Stent System, AngioDynamics Division of E–Z–EM, Inc., Sep., 1994.
Gianturco–Roubin Flex–Stent Coronary Stents, Cook Cardiology, 1995 (brochure).
Medtronic WIKTOR GX, Medtronic Interventional Vascular, no date (brochure).
Miscellaneous literature regarding PS stent, no date.
Miscellaneous literature regarding stent, no date.
Miscellaneous literature regarding Wiktor Stents, no date.
Miscellaneous literature regarding Wallstent, no date.
Donald S. Daim, MD, "New Stent Designs," 2 pages, dated Aug. 1995.

*Primary Examiner*—Michael J. Milano
*Attorney, Agent, or Firm*—Rosenblatt & Redano, P.C.

[57] ABSTRACT

A flexible stent is disclosed that can be constructed in a variety of ways. It can be made from a continuous wire formed into discrete rings of undulating bends where the end rings are closed up on themselves, and the continuous wire which forms the rings between the end rings defines longitudinal gaps in each of the internal rings, which gaps are in turn straddled by crossties which, in the preferred embodiment, extend in a perpendicular plane to the longitudinal axis of the stent, while being disposed in alignment with the cylindrical surface defined by the stent. The crossties act to keep the opening in the inner rings constrained during expansion of the stent. The presence of the longitudinal openings in the internal rings adds to the flexibility of the stent to ease delivery to the desired location. Alternatively, the flexible stent can be etched from a tube. In this preferred embodiment, alternating rings of an undulating wire-type element, etched from a tube, are presented. The rings alternate between those that are fully closed upon themselves, interspersed adjacent those that have a longitudinal opening, coupled by crossties which extend symmetrically from opposite sides and opposite ends of the longitudinal opening in the open rings to attach to the ring above and ring below. The disposition of the crossties helps the stent expand by providing resistance to opening of the longitudinal gap during expansion. The presence of the longitudinal gap adds to the flexibility of the stent for proper delivery to the desired location.

20 Claims, 2 Drawing Sheets

U.S. PATENT DOCUMENTS

| | | |
|---|---|---|
| 4,969,458 | 11/1990 | Wiktor . |
| 4,990,151 | 2/1991 | Wallsten . |
| 5,015,253 | 5/1991 | MacGregor . |
| 5,019,090 | 5/1991 | Pinchuk . |
| 5,041,126 | 8/1991 | Gianturco . |
| 5,100,429 | 3/1992 | Sinofusky et al. . |
| 5,108,416 | 4/1992 | Ryan et al. . |
| 5,133,732 | 7/1992 | Wiktor . |
| 5,139,480 | 8/1992 | Hickle et al. . |
| 5,158,548 | 10/1992 | Lau et al. . |
| 5,160,341 | 11/1992 | Brenneman et al. . |
| 5,163,951 | 11/1992 | Pinchuk et al. . |
| 5,163,952 | 11/1992 | Froix . |
| 5,163,958 | 11/1992 | Pinchuk . |
| 5,183,085 | 2/1993 | Timmermans . |
| 5,195,984 | 3/1993 | Schatz . |
| 5,197,978 | 3/1993 | Hess . |
| 5,213,561 | 5/1993 | Weinstein et al. . |
| 5,222,969 | 6/1993 | Gillis . |
| 5,222,971 | 6/1993 | Willard et al. . |
| 5,234,457 | 8/1993 | Andersen . |
| 5,236,447 | 8/1993 | Kubo et al. . |
| 5,258,042 | 11/1993 | Mehta . |
| 5,266,073 | 11/1993 | Wall . |
| 5,282,823 | 2/1994 | Schwartz et al. . |
| 5,282,824 | 2/1994 | Gianturco . |
| 5,287,861 | 2/1994 | Wilk . |
| 5,292,331 | 3/1994 | Boneau . |
| 5,304,121 | 4/1994 | Sahatjian . |
| 5,304,200 | 4/1994 | Spaulding . |
| 5,306,294 | 4/1994 | Winston et al. . |
| 5,314,472 | 5/1994 | Fontaine . |
| 5,334,201 | 8/1994 | Cowan . |
| 5,336,518 | 8/1994 | Narayanan et al. . |
| 5,342,348 | 8/1994 | Kaplan . |
| 5,344,426 | 9/1994 | Lau et al. . |
| 5,354,308 | 10/1994 | Simon et al. . |
| 5,354,309 | 10/1994 | Schnepp-Pesch et al. . |
| 5,360,401 | 11/1994 | Turnland . |
| 5,368,566 | 11/1994 | Crocker . |
| 5,370,683 | 12/1994 | Fontaine . |
| 5,370,691 | 12/1994 | Samson . |
| 5,383,928 | 1/1995 | Scott et al. . |
| 5,389,106 | 2/1995 | Tower . |
| 5,391,172 | 2/1995 | Williams et al. . |
| 5,397,355 | 3/1995 | Marin et al. . |
| 5,403,341 | 4/1995 | Solar . |
| 5,405,377 | 4/1995 | Cragg . |
| 5,421,955 | 6/1995 | Lau et al. . |
| 5,423,885 | 6/1995 | Williams . |
| 5,433,706 | 7/1995 | Abiuso . |
| 5,437,632 | 8/1995 | Engleson . |
| 5,439,444 | 8/1995 | Anderson et al. . |
| 5,439,445 | 8/1995 | Kontos . |
| 5,441,515 | 8/1995 | Khosravi et al. . |
| 5,443,496 | 8/1995 | Schwartz et al. . |
| 5,443,500 | 8/1995 | Sigwart . |
| 5,449,373 | 9/1995 | Pinchasik et al. . |
| 5,480,423 | 1/1996 | Ravenscroft et al. . |
| 5,496,365 | 3/1996 | Sgro . |
| 5,507,767 | 4/1996 | Maeda et al. . |
| 5,527,354 | 6/1996 | Fontaine et al. . |
| 5,540,712 | 7/1996 | Kleshinski et al. . |
| 5,540,713 | 7/1996 | Schnepp-Pesch et al. . |
| 5,545,211 | 8/1996 | An et al. . |
| 5,549,662 | 8/1996 | Fordenbacher . |
| 5,554,181 | 9/1996 | Das . |
| 5,556,413 | 9/1996 | Lam . |
| 5,562,697 | 10/1996 | Christiansen . |

FLEXIBLE STENT

FIELD OF THE INVENTION

The field of this invention relates to vascular stents that can be delivered to a predetermined position and allowed to spring outwardly or, in the alternative, which can be expanded in place.

BACKGROUND OF THE INVENTION

Vascular stents are structures that are designed to maintain the patency of a vessel in the body. The stent provides internal support to allow the circulation to proceed therethrough. Stents can be used in the vascular system in ureters, bile ducts, esophagus, and in many other tubular structures in the human body.

Stents can be tubular or can be made from wire. Stents are typically made from a metal or polymeric substance or a metal coated with polymers which are biocompatible or contain heparin to reduce blood clotting or other tissue reactions. Many prior designs have used a coil approach where a wire is helically wound on a mandrel. Yet other designs have evolved—braided wire mesh and angulated wire forms wrapped on a spindle to form a coil.

U.S. Pat. No. 5,292,331 by Boneau and U.S. Pat. No. 5,403,341 describe such wire forms. These devices have very poor radial support to withstand the hoop strengths of the artery or vein and further are not suitable for arteries that are bent or curved or for long lesions; multiple stents are required. These designs do not provide any support to hold the wall of the artery, other than the memory of the metal.

Wall Stent, produced by Pfizer Inc., is a braided wire tube. Although this stent is flexible so as to be placed in curved arteries or veins and other body cavities, it does not have any radial strength imparted to it by design.

Wiktor, U.S. Pat. Nos. 4,649,922; 4,886,062; 4,969,458; and 5,133,732 describe a wire form stent. He describes stents made of wire helix made of a preformed wire which is in the sinusoidal form, in which either all or some of the adjacent strands are connected.

Arthus Fontaine, U.S. Pat. No. 5,370,683, also describes a similar device where a flat wire form of sinusoidal shape is wound on a mandrel to form a helical coil. the wire bends are "U" shaped and are connected to alternate "U"-shaped bands.

Allen Tower, U.S. Pat. Nos. 5,217,483 and 5,389,106 describes a similar device where the wire is preformed to a sinusoidal shape and subsequently wound on a mandrel to form a helical coil.

All of the above-described art fails to provide radial support. The preshaped wire form (sinusoidal in most of the prior art) is wrapped on a mandrel to form a coil. However, the forces imported by the vessel wall's hoop strength are radially inward. In other words, the force is acting perpendicular to the plane of the U-shaped wire form. This means that the bends that are in the wire add no structural strength to the wire form to support the force produced by the wall, which is radially inward.

When we examine the simple coils, such as taught in U.S. Pat. Nos. Scott 5,383,928 or Gene Samson 5,370,691 or Rolando Gills 5,222,969, it is apparent that the spring coil will withstand substantial radial forces due to the vessel wall; however, all these stents are bulky in their pre-expanded form and are hard to place in small and curved arteries or veins of the body. Also, a major disadvantage of this design is that when the coil stent is placed in a curved artery or vein, it forms an "accordion" shape whereby some strands in the outer radius are spread and those of the inner radius are gathered. Spring coils can also "flip" to form a flat structure when a longitudinal force is applied on one side of the stent.

The other types of stents that have been developed are tube stents. Palmer, U.S. Pat. Nos. 4,733,665; 4,739,762; 7,776,337; and 4,793,348 describe such a tube stent of slotted metal tube. The slotted metal tube is expanded by a high-pressure balloon to implant the stent into the inside wall of the artery or vein.

Joseph Weinstein, U.S. Pat. No. 5,213,561 describes a similar stent made of tubular materials with slots cut into it. On expansion using a balloon, it forms a structure with diamond-shaped slots.

Henry Wall, U.S. Pat. No. 5,266,073 also describes a stent, tubular, that has slots machined into it. When expanded, the edges of the stent lock to form a cylinder. Not only is this device stiff and can only be used for short lesions, but also the diameter cannot be adjusted to meet the exact needs of the particular vessel but it is fixed to the predetermined sizes.

Lau and Hastigan, U.S. Pat. No. 5,344,426 describes a slotted tubular stent that has a structure similar to Henry Wall's but has provided prongs that will lock in as the stent is expanded.

Michael Marin, U.S. Pat. No. 5,397,355 also describes a tubular slotted stent with locking prongs.

U.S. Pat. No. 5,443,500 illustrates the use of square openings with rectangular prongs that stick therethrough to lock the stent. This design, as well as other locking mechanisms, generally have resulted in very stiff stents because of the use of a tubular-type grid construction. Further, the locking devices have resulted in sharp outwardly oriented tabs which are used for the locking, which could cause vascular damage.

All the above-described tube stents, although typically providing substantial radial support when expanded, are not flexible enough to be placed in curved vessels. Arteries and veins in the human body are mostly curved and are tapered. As such, these tube stents suffer from this main disadvantage.

European patent document 042172982 employs wires that are doubled up and whose ends are snipped off to make a given joint. Such doubling up at the junction of two elements with snipped off free ends creates a potential puncture problem upon radial expansion. The sheer bulk of the doubled up wires makes them rotate radially outwardly away from the longitudinal centerline of the stent, while the plain ends on such an arrangement which are snipped off offer the potential of sharp points which can puncture or damage the intima. On the other hand, the apparatus of the present invention, employing sharp angles, as defined, avoids this problem in an embodiment which illustrates a continuous wire or wire-like member bent into a sharp angle. This type of structure alleviates the concerns of sharp edges, as well as the tendency of a doubled up heavy joint to rotate outwardly toward the intima upon radial expansion of the stem, as would be expected in the EPO reference 042172982.

Often these stents are layered with polymeric sheaths that are impregnated with biocompatible substances or can be coated with heparin or hydrogel. Most sheath-type coatings reduce endothelial cell growth through the stent, which is a major requirement in successful stenting of body cavities such as arteries and veins.

Several parameters in design of stents are important. Of the more important parameters is the issue of recoil. Recoil deals with the memory of the stent material which, generally speaking, upon expansion in the blood vessel will want to recoil back to its original shape. This can be problematic because it is desirable for the stent, once expanded, to remain in good contact with the vessel wall to avoid longitudinal shifting. Furthermore, any recoil constricts the flow passage and presents a greater portion of the stent in the blood flowpath, thus creating additional complications due to the turbulence which ensues.

Related to the concern regarding recoil is another concern regarding component twist. This phenomenon generally occurs when the cross-sectional area of the components is rectangular, such as when the stent is manufactured from a cylindrical piece which is then cut by lasers or other means to form the particular pattern. Particularly in the honeycombed designs involving the use of square or rectangular element cross-sections, radial expansion of such stents generally results in a twist of the component segments such that they extend into the flowpath in the artery or vein. Again, this causes turbulence which is undesirable.

Related to the problem of recoil or constriction after expansion is the ability of the stent to anchor itself in the vascular wall. An anchoring system that does not cause trauma is a desirable feature not found in the prior art.

Yet other considerations which are desirable in a stent not found in the prior art is the flexibility to be maneuvered around bends in the vascular system, coupled with the ability to conform to a bend without kinking or leaving large open areas. The stents of the present invention have the objective of addressing the issue of recoil, as well as providing an anchoring mechanism to fixate the stent once set. Several of the designs incorporate flexibility to allow the stent to follow a bend or curve in a vascular flowpath while a the same time providing sufficient radial deformation to ensure proper fixation while minimizing angular twisting movements of the stent components to minimize turbulence through the stent.

In a recent article appearing in late 1995, by Dr. Donald S. Baim, entitled "New Stent Designs," a description is given of the ideal endovascular prosthesis. There, Dr. Baim indicates that the ideal stent should have low implantation profile with enhanced flexibility to facilitate delivery. He goes on to say that the stent should be constructed from a noncorrosive, nonthrombogenic radiopaque alloy and have expanded geometry which maximizes radial strength to resist vascular recoil. The ideal stent described by Baim is further described as having a wide range of diameters and lengths. Dr. Baim concludes that it is unlikely that any current designs satisfy all these requirements. Thus, one of the objectives of the present invention is to go further than the prior designs in satisfying the criteria for the ideal designs as set forth by Dr. Baim in his recent article.

SUMMARY OF THE INVENTION

A flexible stent is disclosed that can be constructed in a variety of ways. It can be made from a continuous wire formed into discrete rings of undulating bends where the end rings are closed up on themselves, and the continuous wire which forms the rings between the end rings defines longitudinal gaps in each of the internal rings, which gaps are in turn straddled by crossties which, in the preferred embodiment, extend in a perpendicular plane to the longitudinal axis of the stent, while being disposed in alignment with the cylindrical surface defined by the stent. The crossties act to keep the opening in the inner rings constrained during expansion of the stent. The presence of the longitudinal openings in the internal rings adds to the flexibility of the stent to ease delivery to the desired location. Alternatively, the flexible stent can be etched from a tube. In this preferred embodiment, alternating rings of an undulating wire-type element, etched from a tube, are presented. The rings alternate between those that are fully closed upon themselves, interspersed adjacent those that have a longitudinal opening, coupled by crossties which extend symmetrically from opposite sides and opposite ends of the longitudinal opening in the open rings to attach to the ring above and ring below. The disposition of the crossties helps the stent expand by providing resistance to opening of the longitudinal gap during expansion. The presence of the longitudinal gap adds to the flexibility of the stent for proper delivery to the desired location.

DETAILED DESCRIPTION OF THE PREFERRED EMBODIMENT

Figure 1:
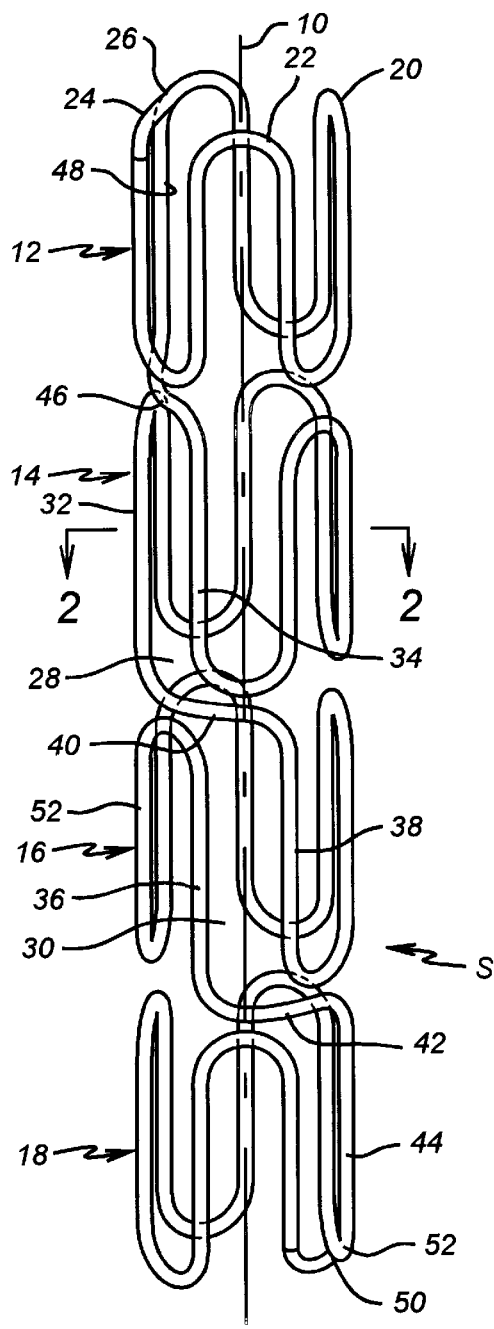
FIG. 1 is a perspective view of one embodiment of the stent made from bent wire.
Figure 5:
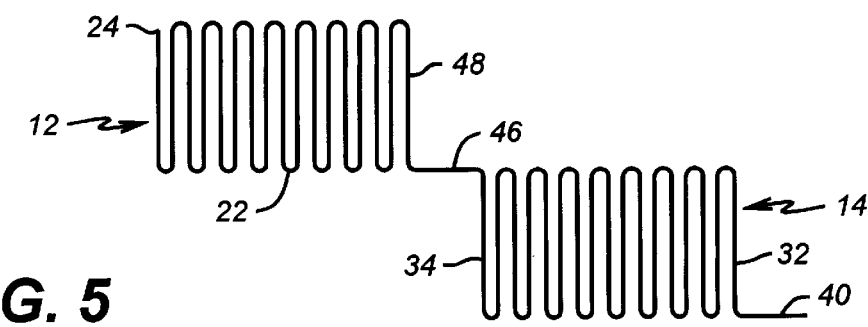
FIG. 5 is a flattened view of the stent shown in FIG. 1, showing a portion of the stent prior to its being wrapped on a mandrel.

A first embodiment of the stent S of the present invention is shown in FIGS. 1 and 5. In FIG. 1, the stent is assembled into a tubular shape, having a longitudinal axis 10. Wrapped around the longitudinal axis 10 is a series of rings 12, 14, 16, and 18. Generally, rings 12 and 18 will be referred to as the end rings. Those skilled in the art will appreciate that varying amounts of intermediate rings, such as 14 and 16, can be used without departing from the spirit of the invention.

A continuous wire member 20, having any desired cross-sectional shape, is bent into an undulating pattern made up by a series of generally U-shaped segments 22. The end 24 of ring 12 is brought around and attached at point 26 to one of the U-shaped segments on ring 12 so as to close off ring 12 from having any longitudinal gaps. This is to be distinguished from the intermediate rings, such as 14 and 16, which each have a longitudinal gap 28 and 30, respectively. To better see the gaps in rings 14 and 16, the gap 28 is defined between segments 32 and 34, while the gap 30 is defined between segments 36 and 38. Referring to FIG. 1, it can be seen that segment 32 is ultimately connected to segment 38 via crosstie 40. Crosstie 40 preferably runs circumferentially following the cylindrical outer shape of rings 14 and 16 but disposed in between them such that crosstie 40, when viewed in the direction of cross-section lines 2—2, has a generally arcuate shape following the tubular shape of the stent S in a perpendicular plane to the longitudinal axis 10. At the lower end of the gap 30 is another crosstie 42, which forms as an extension of segment 36. Ultimately, crosstie 42 becomes segment 44 in end ring 18. With regard to opening 28, a crosstie 46 is an extension of segment 34 and finally extends and becomes segment 48 of end ring 12.

In the preferred embodiment, the crossties follow the outer contours of the stent S, thus they have an arcuate shape. Pairs of crossties extend from opposed ends of a given opening. For example, with regard to longitudinal opening 30, crosstie 40, upon expansion of the stent S with a device such as a balloon, will pull in a clockwise direction on segment 38, while crosstie 42 will pull in a counterclockwise direction on segment 36. These opposing pulls from opposite sides of the gap 30 tend to hold the gap 30 from increasing significantly in size during expansion with a balloon. As a result, the undulating segments of ring 16, upon expansion of the stent S with a balloon or other device, will expand for setting the stent without appreciable increase in width of opening 30. However, the presence of opening 30, or opening 28 in ring 14, or any other longitudinal opening in an interior ring to the stent S, is to allow the stent to have greater flexibility during insertion. The longitudinal openings in the intermediate rings, such as 14 and 16, can be located on the stent S in longitudinal alignment or they can be offset, as shown in FIG. 1.

In the preferred embodiment, the end rings 12 and 14 do not have loose ends but rather have the end of the wire which forms the stent S rejoined to one of the undulating bends in that ring. Accordingly, the lower end ring 18 has an end 50, which is reconnected to a reversing U-type bend 52. It should be noted that while U-type undulating bends have been described in FIG. 1, different configurations for the individual rings, such as 12, 14, 16, and 18, can be employed without departing from the spirit of the invention. The undulating bends, such as 22, can comprise of segments that approach each other and come to a point or meet in some other fashion. The individual rings can also have diamond shapes. The significant feature of the stent is that the end rings close on themselves but retain a generally flexible structure to facilitate fixation by radial expansion, while the intermediate rings have a longitudinal opening characterized by crossties which create opposing forces on the opening to resist enlargement of the longitudinal opening upon radial expansion of the stent S when placed in position. In the preferred embodiment, the crossties have arcuate shapes and follow the profile of the stent S between adjacent rings, such as 14 and 16, such that they present opposing clockwise and counterclockwise forces from opposed ends of the opening to resist enlargement of the opening or gap while a given ring expands.

Thus, the preferred structure is illustrated, for example, by looking at longitudinal opening or gap 30 in ring 16, which is held against expansion when the stent is expanded by virtue of crossties 40 and 42. Crosstie 40 is on one side and one end of the longitudinal opening 30 and exerts a clockwise force, while crosstie 42 is on the opposite side and opposite end of opening 30 and exerts a counterclockwise force. The combination of the forces exerted by crossties 40 and 42 in opposed directions along the profile of the stent S helps to keep the opening 30 from significantly enlarging as the distance between other segments of ring 16, which form undulating bends, expand when the stent S is set. Thus, for example, in ring 16, the distance between segment 36 and segment 52 will increase as measured circumferentially when the stent S is expanded to a significant degree beyond any change to the circumferential distance between segments 36 and 38 which define the longitudinal gap 30.

FIG. 5 illustrates how the stent of FIG. 1 can be produced. It is understood that FIG. 5 is only a partial rendition of the stent shown in FIG. 1. Referring to FIG. 5, end 24 is illustrated for ring 12. Crosstie 46 presents the transition from segment 48, which is the last segment in ring 12, and segment 34, which is the first segment in ring 14. Thus, when the wire structure of FIG. 5 is rolled around a mandrel (not shown), the longitudinal opening 28 in ring 14 will be defined between segments 32 and 34, as shown in FIG. 1. FIG. 5 also shows crosstie 40, which becomes an extension of segment 32. By controlling the size of the reversing bends 22 and the length of the crosstie 46, the longitudinal gaps, such as 28 and 30, can be disposed in a circumferentially offset manner as shown in FIG. 1 or in a different pattern, such as in alignment with each other.

Figure 2:
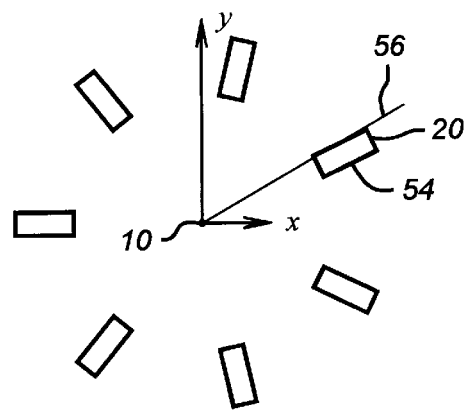
FIG. 2 is a sectional view along lines 2—2 of FIG. 1.

The cross-section of the wire material 20 can be round; however, other cross-sectional shapes can be used. To the extent an unsymmetrical cross-sectional shape is used for the wire 20, such as a rectangle, FIG. 2 illustrates a preferred orientation for the rectangular cross-section. FIG. 2 is a section view along lines 2—2 of FIG. 1 and illustrates the longitudinal axis 10 with the cross-sections of the wire having their longer sides 54 in alignment with a radius 56 extending from the longitudinal axis 10. By orienting the wire so that its long side 54 is in alignment with a radial line 56, additional benefits are obtained. The stent is made easier to flex radially such as when expanded by a balloon. This improves the results from use of the stent so that it is securely implanted. Additionally, orientation of the long dimension of the wire 20, in alignment with a radial line 56, facilitates the advancement of the stent to the position where it is to be deployed. As shown in FIG. 2, the stent S can flex more easily along the X and Y directions while it is being advanced with the long sides 54 in alignment with a radial line, such as 56.

It is also within the scope of the invention to include one or more closed intermediate rings in the design of FIG. 1.

Figure 3:
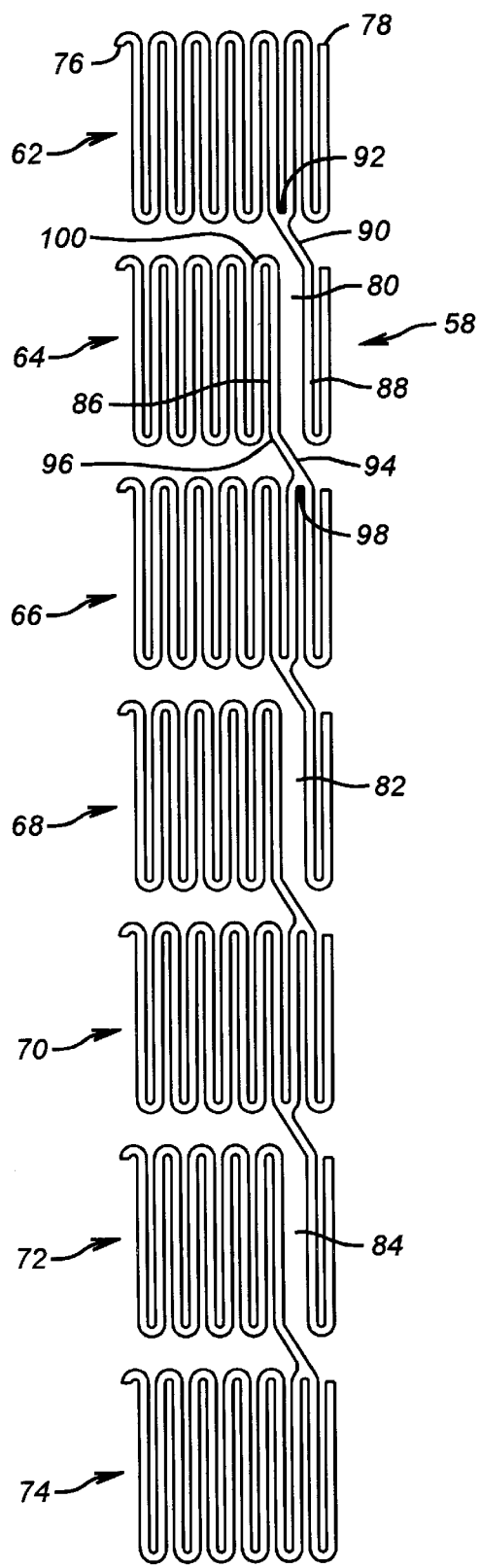
FIG. 3 is a flattened view of an alternative embodiment, illustrating alternating closed and open rings, with diagonally oriented crossties.
Figure 4:
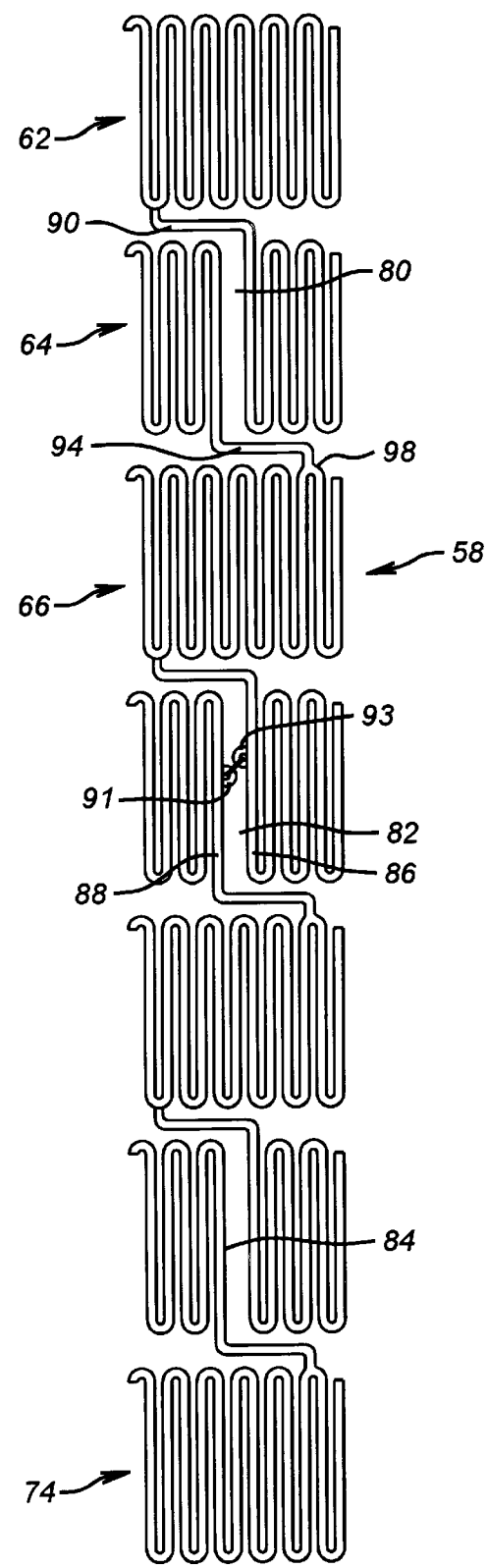
FIG. 4 is the design shown in FIG. 3, with a different arrangement for the crossties.

While the stent shown in FIGS. 1 and 5 can be preferably fabricated from bending a wire, the stent shown in FIGS. 3 and 4 is amenable to being etched from a tube by known techniques. In the preferred embodiment of the invention as shown in FIG. 3, the stent 58 is shown in flattened form. It has a series of rings 62, 64, 66, 68, 70, 72, and 74. Those skilled in the art can appreciate that it can have any number of rings depending on the application, which is different than the number illustrated in FIG. 3 without departing from the spirit of the invention. Since the drawing in FIG. 3 is in flattened form, those skilled in the art will appreciate that end point 76 is, in fact, not an end point but is joined to what is shown as end point 78 (which is also not an end point when the tube is etched to make a three-dimensional stent on a mandrel). In essence, when the stent is made, what are shown in the drawing as end points 76 and 78 are not, in fact, end points but a continuation of the ring structure that makes up ring 62. In similar respects, the other rings illustrated in FIG. 3 are, in fact, unitary. What can readily be seen by examining FIG. 3 is that the end rings 62 and 74 have no longitudinal openings or gaps, while the interspersed rings 64, 68, and 72 each, respectively, have longitudinal openings or gaps 80, 82, and 84. While the openings 80, 82, and 84 are in longitudinal alignment in FIG. 3, they can be circumferentially misaligned when the stent structure 58 is formed without departing from the spirit of the invention. In the design of FIG. 3, as a typical example, the longitudinal opening 80 is formed by segments 86 and 88. An extension of segment 88 is diagonal crosstie 90, which ultimately joins a circumferentially offset U-bend 92 in ring 62. At the opposite side and opposite end of longitudinal opening 80, segment 86 continues as crosstie 94, which is bent preferably at about 45° at point 96 so that it joins U-bend 98 at a location circumferentially offset from opening 80. Thus, in the embodiment of FIG. 3, the crossties 90 and 94 link to the ring above and below, respectively, but at a circumferentially offset point. As a result, crosstie 90, when the stent 58 is expanded, puts a clockwise force on segment 88, while crosstie 94, when the stent 85 is radially expanded, puts a counterclockwise force on segment 86. The net result of the crossties 90 and 94 is to apply a closing force to segments 86 and 88, which make up the longitudinal opening 80, so that there is a greater resistance to growth of the opening 80 than there is to the widening of an individual set of return bends, such as 100. In a similar manner, the longitudinal openings 82 and 84 are impacted by their crossties from above and below. As seen by comparing FIGS. 3 and 4, and angular disposition of the crossties, such as 90 and 94, can employ more severe angles, such as about 90° to longitudinal axis 10, such that the crossties are literally disposed between individual rings, such as 62 and 64, for example. In FIG. 4, the crossties 90 and 94 have a generally arcuate shape and follow the tubular profile of the stent 58. As shown in FIG. 4, the crosstie 94 spans three return bends on ring 66 before being joined at U-bend 98. Thus, the concepts in the designs of FIGS. 3 and 4 are similar, with the difference being that the crossties, typically such as 90 and 94, exert greater closing forces on the longitudinal gaps, such as typically 80, while the stent 58 is being radially expanded. Also, tabs 91 and 93 can be placed on the members 86 and 88, and can be joined using a crosstie, such as thread, string, or wire made of metal or plastic. Although shown in one location in FIG. 4, it can be in all locations where a gap or opening such as 82 is disclosed.

While alternating closed rings and rings with gaps are disclosed in FIGS. 3 and 4, different patterns can be employed without departing from the spirit of the invention. Thus, more than one closed ring can be adjacent to another closed ring and, likewise, adjacent rings can have longitudinal gaps. The preferred embodiment of the stent 58 is as shown in FIG. 4, where the end rings 62 and 74 are of an undulating wire-like material with U-bends and are closed, with an alternating pattern of intermediate rings which are closed and those which have longitudinal openings, in combination with crossties which extend from opposite sides and opposite ends of the longitudinal openings so as to create opposing closing forces on the longitudinal openings. This, in turn, allows the rings with the longitudinal openings to expand radially at similar rates to the end rings, such as 62 and 74, when the stent 58 is expanded. In essence, the U-bends, such as 98, grow larger to set the stent 58 while the crossties, such as 90 and 94, hold the longitudinal openings, such as 80, to a relatively stable dimension.

In the preferred embodiment of FIG. 4, the longitudinal openings, such as 80, 82, and 84, are in alignment. Offset arrangements of the longitudinal openings are also within the scope of the preferred embodiment. As with the design of FIG. 1, the presence of the longitudinal openings, such as 80, 82, and 84, gives the stent 58 flexibility along its length in a variety of planes so that it can traverse tortuous passages to arrive at the location where it is to be expanded. The thickness of the material, which is used as the initial tube for etching to create the shapes shown in FIGS. 3 and 4, determines whether the cross-sectional area is symmetrical or asymmetrical. If it is asymmetrical, it is preferred that the cross-section of the individual wire-like segments, such as 86 and 88, is disposed in the manner shown in FIG. 2, where the longer dimension, such as 54, is in alignment with one of the radial lines, such as 56.

Those skilled in the art will appreciate that what has been disclosed is a stent that has flexibility for insertion, as well as a design which allows reliable radial expansion of the stent when it is located in the desired position. Whether the stent is manufactured of a wire that is continuously bent, or etched from a cylinder using known techniques, the presence of the longitudinal openings provides the desired flexibility for insertion, while at the same time the crossties, and the manner in which they are disposed with regard to the longitudinal openings, provide sufficient resistance to hoop stresses so that the reversing bends of a given ring, which has the longitudinal opening, will preferentially expand for setting the stent while the dimensions of the longitudinal openings, which had heretofore provided flexibility for advancement of the stent, are held in a relatively stable relationship to each other.

The foregoing disclosure and description of the invention are illustrative and explanatory thereof, and various changes in the size, shape and materials, as well as in the details of the illustrated construction, may be made without departing from the spirit of the invention.

I claim:

1. A flexible stent, comprising:

a plurality of rings forming a generally cylindrical shape about a longitudinal axis;

each said ring connected to an adjacent ring by a crosstie;

at least one first ring being one of said rings and formed having a gap which extends generally in the direction of the longitudinal axis and having crossties which extend from opposing segments of said ring which define said gap, respectively, to a ring above and a ring below in a manner which resists enlargement of the gap as the ring which defines said gap is radially expanded.

2. The stent of claim 1, wherein:

said crossties on said first ring conform to the cylindrical shape defined by said rings, said first ring having a top and a bottom;

a first crosstie is connected near the top of said first ring on one side of the gap, and a second crosstie is connected to said first ring near its bottom and on the opposite side of said gap.

3. The stent of claim 2, wherein:

said first and second crossties are oriented angularly at about 45° to the longitudinal axis.

4. The stent of claim 2, wherein:

said first and second crossties are oriented at about 90° to said longitudinal axis.

5. The stent of claim 2, wherein:

said first and second crossties extending symmetrically with respect to said gap and in opposed directions.

6. The stent of claim 5, wherein:

the rings on either end of the stent are closed and at least one said first ring with a gap is disposed in between.

7. The stent of claim 6, wherein:

a plurality of intermediate rings between said rings on either end where at least some intermediate rings have a gap and some of said gaps are longitudinally aligned.

8. The stent of claim 6, wherein:

a plurality of intermediate rings between said rings on either end where at least some intermediate rings have a gap and some of said gaps are longitudinally misaligned.

9. The stent of claim 6, wherein:

said rings are disposed in a layout where at least some of the rings which are closed are juxtaposed with rings with gaps.

10. The stent of claim 9, wherein:

some of the gaps in the rings are misaligned.

11. The stent of claim 9, wherein:

some of the gaps in the rings are aligned.

12. The stent of claim 6, wherein:

said rings are formed of a wire-like member, bent in an undulating pattern which defines said generally cylindrical shape, said undulations formed by segments which move away from each other as said rings are radially expanded to fixate the stent;

said gap is defined by two such opposed segments of a given ring and said first and second crossties create opposed forces on the segments defining said gap to resist expansion of said gap as the segments forming the undulations of a given ring move away from each other when the stent is fixated.

13. The stent of claim 12, wherein:

said wire-like member has an asymmetrical cross-section having a long dimension which, when viewed in a plane perpendicular to the longitudinal axis, is generally aligned with a radial line extending from the longitudinal axis.

14. The stent of claim 6, wherein:

a plurality of intermediate rings between said rings on either end where each intermediate ring has a gap and some of said gaps are longitudinally misaligned.

15. The stent of claim 6, wherein:

said rings are disposed in a pattern where rings which are closed alternate with rings with gaps.

16. The stent of claim 13, wherein:

a plurality of intermediate rings between said rings on either end where each intermediate ring has a gap and some of said gaps are longitudinally misaligned.

17. The stent of claim 13, wherein:

said rings are disposed in a pattern where rings which are closed alternate with rings with gaps.

18. The stent of claim 17, wherein:

some of the gaps in the rings are aligned.

19. The stent of claim 18, wherein:

said first and second crossties are oriented angularly at about 45° to the longitudinal axis.

20. The stent of claim 18, wherein:

said first and second crossties are oriented at about 90° to said longitudinal axis.

* * * * *